United States Patent [19]

Flament

[11] 3,968,212

[45] July 6, 1976

[54] ORGANOLEPTIC CYCLOPENTAPYRAZINES AS FLAVORING AGENTS

[75] Inventor: Ivon A. Flament, Geneva, Switzerland

[73] Assignee: Firmenich S.A., Geneva, Switzerland

[22] Filed: Apr. 23, 1975

[21] Appl. No.: 570,802

Related U.S. Application Data

[62] Division of Ser. No. 409,016, Oct. 23, 1973, Pat. No. 3,920,647.

[30] Foreign Application Priority Data

Oct. 26, 1972 Sweden.............................. 15690/72

[52] U.S. Cl........................... 424/250; 260/250 BC; 426/537
[51] Int. Cl.² ...................................... A61K 31/495
[58] Field of Search ..:.......... 260/250 BC; 424/250; 426/537

[56] References Cited
UNITED STATES PATENTS

| 2,400,398 | 5/1946 | Dixon | 260/250 BC |
| 2,945,858 | 7/1960 | Tarailo | 260/250 B |
| 3,647,792 | 3/1972 | Evers et al. | 260/250 BC |
| 3,686,177 | 8/1972 | Pittett et al. | 260/250 BC |
| 3,705,121 | 12/1972 | Pittett et al. | 260/250 BC |
| 3,881,025 | 4/1975 | Flament | 260/250 BC |
| 3,920,647 | 11/1975 | Flament | 260/250 BC |

OTHER PUBLICATIONS

Polak's Frutal Works N.V. et al., Chemical Abstracts, vol. 71, 61421a (1969).

Primary Examiner—Nicholas S. Rizzo
Assistant Examiner—Jose Tovar
Attorney, Agent, or Firm—Pennie & Edmonds

[57] ABSTRACT

New pyrazine derivatives and their use as flavouring and taste-modifying agents in the aromatization of foodstuffs in general and imitation flavours for foodstuffs, beverages, animal feeds, pharmaceutical preparations and tobacco products.

1 Claim, No Drawings

ORGANOLEPTIC CYCLOPENTAPYRAZINES AS FLAVORING AGENTS

This is a division of application Ser. No. 409,016 filed Oct. 23, 1973, now U.S. Pat. No. 3,920,647 issued 11-18-75.

SUMMARY OF THE INVENTION

The compounds to which the present invention relates belong to the class of cycloaliphatic pyrazine derivatives having the formula

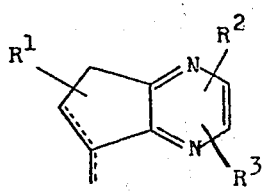

I containing a double bond at one of the positions indicated by the dotted lines and wherein each of the substituents $R^1$, $R^2$ and $R^3$ represents a hydrogen atom or an alkyl radical containing from 1 to 6 carbon atoms.

The compounds of formula I possess interesting organoleptic properties and as a consequence may be conveniently used in the flavour industry.

BACKGROUND OF THE INVENTION

One of the main objects of the aromatization of foodstuffs for instance is to restore the original quality and nature of the flavour, aroma and taste of a given foodstuff material. Very often in fact the organoleptic properties of foodstuffs particularly diminish or are somehow modified in the course of the processes of freezing and storage, or during the modifications, such as cooking or baking, to which the foodstuffs are subjected in order to yield an edible material.

In the past the aromatization was mainly achieved by using materials of natural origin. Nowadays, however, synthetic chemical compounds are used at an ever increasing rate. Said compounds possess the advantage of being available very often in unlimited quantities and at prices lower than those of the natural materials. Moreover, due to the fact that the flavouring character of a natural material is the result of the overall effect determined by the combination and interaction of each of its constituents, the effects achieved by said natural material are very often not as well reproducible as those obtained by the use of the pure synthetic compounds.

As a consequence, the probelm that the chemical industry has to solve is to satisfy the increasing demand of organoleptically interesting chemicals in order to better suit the specific needs of the flavourists.

PREFERRED EMBODIMENTS OF THE INVENTION

Among the great variety of flavour notes currently sought by the flavourists, specifically in connection with the aromatization of meat, meat-containing or meat-simulating materials, the burnt, animal note has been particularly investigated. The present invention provides a novel solution to this problem.

One of the main objects of this invention is in fact to provide flavouring compositions which comprise as active ingredient at least one of the pyrazine derivatives of formula I.

Another object of the present invention is to provide a method for modifying, improving or enhancing the flavouring properties of artificial flavouring compositions or those of foodstuffs for human and animal comsumption, beverages, pharmaceutical preparations and tobacco products.

A further object of the present invention is to provide a foodstuff, a beverage, a pharmaceutical preparation or a tobacco product which comprises having added thereto a small but flavouring effective amount of at least one of the compounds of formula I.

Particularly it has now been found that a meaty flavour can be enhanced or imparted to a foodstuff which contains meat or a meat simulating product by the incorporation of certain pyrazine derivatives. Accordingly, the present invention provides a foodstuff comprising a meat product or a meat simulating product and a pyrazine derivative of formula I.

The pyrazine derivative may be incorporated as such, or in the form of precursors or reactants yielding the derived compound after completion of the process used for making the foodstuff ready for consumption. It can be added to the products to be flavoured during any step in the course of treatments they may undergo, preferably before or immediately after cooking.

The compounds of formula I may be used in the flavour industry on their own, or in compositions comprising one or more flavouring compounds in diluted or concentrated solution in the solvents currently used in the art such as, e.g. ethyl alcohol, triacetine or diethyleneglycol.

Depending on the nature of the other constituents of a given composition or of that of the products to which they are added, the compounds of formula I can develop the organoleptic characters typical of certain cereals particularly of freshly torrefied cereals such as barley or maize for example, or of certain fruits such as nuts, hazel-nuts or peanuts, particularly when these fruits are previously toasted.

The compounds of the invention may equally develop the typical animal notes of grilled meat. These organoleptic characters are particularly suitable for imparting an improved meaty taste and flavour to meat or meat-simulating products such as gluten, casein, soybean proteins and the like or meat hydrolysates. The compounds of formula I may be conveniently used for the flavouring of meat concentrated gravy, canned meat, sauces, canned concentrated soups, seasoning compositions and the like.

We have equally found that the compounds of formula I may be used for the aromatization of beverages and foodstuffs containing coffee or cocoa. The grilled and roasted notes developed by said products are sharply enhanced by incorporating thereto a small amount of the compounds of the invention.

The proportions in which the flavouring agents of formula I are used in flavouring compositions or in foodstuffs, beverages, pharmaceutical preparations or tobacco products can vary widely, depending on the specific organoleptic effect it is desired to achieve and the type of material to which they are added.

Interesting flavouring effects can be achieved with amounts ranging from 0.1 to 100 ppm, preferentially from about 1 to 10 ppm, based on the total weight of the flavoured material. The said proportions may however be increased, namely when special flavouring effects are desired. When the compounds of formula I are used as ingredients in flavouring compositions, the proportions therein may be increased up to about 5% of the weight of the flavouring compositions.

In all cases, the ranges mentioned above may be varied, in order to achieve specific organoleptic effects.

Among the compounds of formula I which can be used according to the invention, the following two are of particular interest:

5-methyl-7(H)-cyclopenta[b]pyrazine and 5-methylene-6,7-dihydro-cyclopenta[b]pyrazine of formula

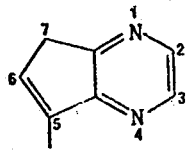 and 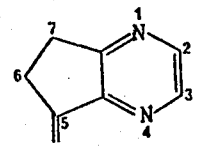

respectively.

Although some of the compounds of formula I have a structure similar to that of certain pyrazine derivatives already described in the scientific literature [cf.: J. Agr. Food Chem., 19, 972 (1971)], in Dutch patent specification 68 12899 and the German patent specification No. 2,117,926, laid open to public inspection on Mar. 13, 1969 and Nov. 4, 1971, respectively, we have found that their flavouring characteristics are quite different. This fact illustrates once more the character of unpredictability inherent to any research in the field of flavours.

So far, in fact, no precise correlation has been found between the chemical structure of a given compound and its organoleptic properties.

In particular, we have observed that the compounds of formula I possess an extremely high flavouring power, clearly higher than that displayed by the known analogues It has to be understood however that the flavouring characters of a given compound may be appreciated at a different degree by different tasters and namely depend upon the nature of the coingredients in a given composition.

An additional object of this invention is to provide a process for preparing the compounds of formula I, said process comprising a dehydrogenation of a compound of formula

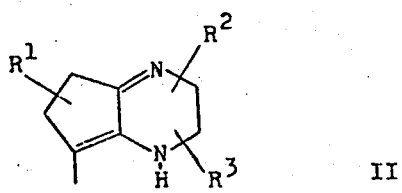

wherein the symbols $R^1$, $R^2$ and $R^3$ have the meaning aforementioned.

According to a preferred embodiment of the process of the present invention, the said dehydrogenation may be effected in the presence of a catalyst essentially consisting of copper chromite of formula $CrCr_2O_4$ and at a temperature ranging from about 250° to 350°C, preferably in the vicinity of 300°C.

The dehydrogenation can be carried out by passing an aqueous solution of the compound of formula II through the bulk catalyst previously heated to and kept at the required temperature.

The desired compounds of formula I are thus obtained as constituents of a mixture essentially comprising the pyrazine derivatives of formulae

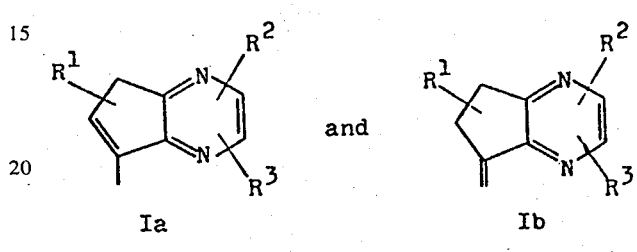

Ia and Ib (wherein the symbols $R^1$, $R^2$ and $R^3$ have the meaning defined above).

These compounds can be separated one from the other by applying to the mixture the usual techniques of separation such as e.g. fractional distillation, preferably by means of a spinning band column, or preparative vapour phase chromatography.

The compounds of formula II, used as starting materials in the process of the invention, can be synthetized by condensing a diamine with a cyclopentenolone derivative according to the following reaction scheme [cf. e.g.: German patent specification No. 2,117,926]:

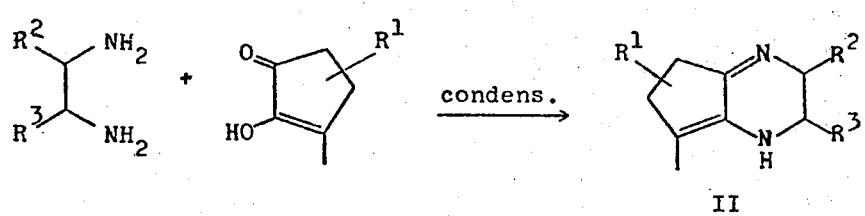

The invention is better illustrated by the following examples wherein the temperatures are given in degrees centigrade and the abbreviations have the meaning usual in the art.

EXAMPLE 1

5-Methyl-7(H)-cyclopenta[b]pyrazine and 5-methylene-6,7-dihydro-cyclopenta[b]pyrazine 100 g of a 25% aqueous solution of 5-methyl-3,4,6,7-tetrahydro-2(H)-cyclopenta[b]pyrazine were passed through a column maintained under reduced pressure and filled up with 125 g of copper chromite heated to 300°. The condensed solution thus obtained was saturated with sodium chloride and extracted with ether. By evaporation of the volatile portions and fractional distillation of the obtained residue under released pressure, there was obtained a product having B.p 90°–125°/12 Torr.

A separation by means of preparative vapour phase chromatography using a APIEZON L column enabled the recovery of:

1. 5-methyl-6,7-dihydro-5(H)-cyclopenta[b]pyrazine: B.p 78°–80°/10 Torr;

IR(CCl$_4$): 3053, 2965, 2930, 2875, 1453, 1432, 1382, 1328, 1148, 1124, 1090, 1074, 1015 and 842 cm$^{-1}$;

NMR (CCl$_4$): 1.30 (3H,d); 1.5–2.0 (1H, m); 2.0–2.5 (1H, m); 2.5–3.5 (m, 3H); 8.14 (2H, s) δ ppm;

MS: 134 (49.2); 133 (26.2); 120 (7.7); 119 (100); 92 (7.2); 80 (3.6); 79(7.2); 78 (14.9); 65 (7.2); 53 (5.1); 52 (9.8); 51 (5); 41 (6.7); 39 (12.3): 27 (7.2).

2. 5-methyl-7(H)-cyclopenta[b]pyrazine:

IR (CCl$_4$): 3055, 2920, 1610, 1546, 1443, 1430, 1390, 1373, 1363, 1338, 1172, 1146, 1093, 1000, 939, 869, 832 cm$_-^1$;

NMR (CCl$_4$): 2.16 (3H); 3.30 (2H); 6.55 (1H); 8.19 (2H) δ ppm;

MS: 133 (10.3); 132 (100); 131 (74.7); 105 (15.5); 104 (31.4); 79 (10.3); 78 (27.8); 77 (26.8); 76 (16.5); 75 (10.3); 74 (8.2); 65 (8.2); 64 (8.2); 63 (11.9); 62 (5.7); 53 (17.0); 52 (48.5); 51 (45.4); 50 (27.3); 41 (6.2); 40 (7.2); 39 (29.4); 38 (15.5); 37 (10.3); 27 (24.2).

3. 5-methylene-6,7-dihydro-cyclopenta[b]pyrazine:

IR (CCl$_4$): 3055, 2925, 1645, 1440, 1429, 1408, 1365, 1150, 1120, 900 and 850 cm$^{-1}$;

NMR (CCl$_4$): 2,98 (4H); 5.21 and 6.01 (2H); 8.22 (2H) δ ppm;

MS: 113 (11.1); 132 (100); 131 (69.6); 105 (14.5); 104 (23.2); 79 (11.1); 78 (22.2); 77 (19.8); 76 (13.5); 75 (8.2); 74 (6.8); 66 (10.6); 65 (11.6); 64 (7.7); 60 (8.7); 53 (14.5); 52 (43.0); 51 (35.7);50 (24.2); 41 (8,7); 40 (10.6); 39 (31.9); 38 (15.0); 37 (8.7); 27 (17.9).

5-Methyl-3,4,6,7-tetrahydro-2(H)-cyclopenta[b]pyrazine, used as starting material in the hereinabove process, can be prepared as follows:

a. To a solution of 100 g (0.89 M) of 3-methyl-2-hydroxycyclopenta-2-enone in 3 l of ether, there was added under vigourous stirring a solution of 53.5 g of ethylenediamine in 400 ml ether. The immediate formation of an abundant precipitate was observed. The reaction mixture was left standing during 30 minutes, then cooled to 0° and filtered. The solid white precipitate thus recovered was then crystallized twice with ether, to yeild 130 g of a product having m.p. 82°–4° (decomposition).

b. 130 g of the product obtained according to the procedure described under letter (a) in 4 l methanol were heated to reflux during 6 h in the presence of 100 g of sodium hydroxide. After evaporation of the volatile portions under reduced pressure, the reaction mixture was subjected to extraction, preferably by means of a Soxhlet extractor, with ether. By the usual treatments of drying over Na$_2$SO$_4$ and evaporation, there was obtained a residue which by fractional distillation under reduced pressure at ca. 0.001 Torr (bath temp. = ca. 95°) gave 33 g (yield 27%) of a product having m.p. 115°–7°. This material was kept under nitrogen at low temperature and in the darkness.

IR (CCl$_4$): 3250, 2958, 2925, 2850, 1664, 1640, 1440, 1426, 1408, 1325, 1216, 1207, 1164, 1101, 991 and 884 cm$^{-1}$;

NMR (DMSO): 1.7 (3H, s); 2.29 (s, broad band, 4H); 2,86 (2H, t); 3,44 (2H, m); 5.06 (1H, s, broad band) δ ppm.

EXAMPLE 2

The two compounds synthetized according to the procedure described in example 1 were subjected to an organoleptic evaluation by a panel of flavour experts.

For carrying out such an evaluation 1 g of a 0.1% ethanolic solution (in 95% ethanol) of the compounds under investigation was added to 1 lt of a 0.5% NaCl solution.

The organoleptic characters of the pyrazinic compounds were defined as follows:

a. 5-methyl-7(H)-cyclopenta[b]pyrazine: strong animal, nutty, meaty note.

b. 5-methylene-6,7-dihydro-cyclopenta[b]pyrazine: animal, burnt, fatty, meaty note

EXAMPLE 3

A flavouring composition imitating beef broth was prepared by dissolving the following ingredients in water (parts by weight):

| | |
|---|---|
| Commercial beef gravy | 100 |
| Monosodium glutamate | 10 |
| Sodium 5-inosinate and sodium guanilate (50:50) | 0.05 |
| Sodium chloride | 80 |
| Lactic acid | 5 |

Further water was added up to a volume of 10 lt.

To 1 lt of the above broth there were added 0.3 g of a 1% ethanolic solution (95% ethyl alcohol) of 5-methyl-7-(H)-cyclopenta[b]pyrazine. There was thus obtained a "test" foodstuff. A "control" foodstuff was prepared by adding an equal amount of 95% ethyl alcohol to 1 lt of the beef broth obtained as described above.

A sample of each of the foodstuffs was subjected to an orgaoleptic evaluation by a panel of flavour experts, who had to determine its value.

The majority of the panel indicated that the "test" foodstuff presented an animal note which was more defined than that of the "control" foodstuff. It possessed moreover a well distinct grilled-meaty note which reminded for certain of its characters the flavour of grilled chicken.

Analogous results were achieved by substituting 5-methylene-6,7-dihydro-cyclopenta[b]pyrazine for 5-methyl-7(H)cyclopenta[b]pyrazine. The foodstuff thus obtained possessed moreover a more intense grilled and burnt note.

EXAMPLE 4

7 g of 1% alcoholic solution of 5-methyl-7(H)-cyclopenta[b]pyrazine (95% ethanol) were sprayed onto 100 g of an "American blend" type tobacco. The tobacco thus flavoured was used to manufacture "test" cigarettes, the smoke of which was then subjected to organoleptic evaluation by comparison with non flavoured cigarettes ("control"). The tobacco used to prepare the "control" cigarettes was preliminarily treated with 95% ethanol.

The panel of experts unanimously defined the taste of the "test" cigarettes as possessing a fuller "body" than that of the "control" cigarettes. It possessed moreover a stronger burnt note.

Analogous effects were observed by using as flavouring ingredient the same proportion of 5-methylene-6,7-dihydrocyclo-penta[b]pyrazine.

I claim:

1. A flavouring composition consisting essentially as an active ingredient at least one of the compounds of formula

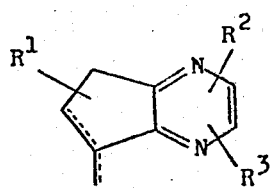
I
having a double bond at one of the positions indicated by the dotted lines and wherein each of the substituents $R^1$, $R^2$, and $R^3$ represents a hydrogen atom or alkyl having from 1 to 6 carbon atoms.
* * * * *

UNITED STATES PATENT AND TRADEMARK OFFICE
CERTIFICATE OF CORRECTION

PATENT NO. : 3,968,212
DATED : July 6, 1976
INVENTOR(S) : Ivon A. Flament

It is certified that error appears in the above-identified patent and that said Letters Patent are hereby corrected as shown below:

Column 1, line 54 "probelm" should be --problem--

Column 4, line 63 "released" should be --reduced--

Column 5, line 12 "869, 832 $cm\_^{1}$" should be --869, 832 $cm^{-1}$--

Column 5, line 24 "NMR ($CCl_4$): 2,98 (4H);" should be --
   NMR ($CCl_4$): 2.98 (4H);--

Column 5, line 26 "MS: 113 (11.1);" should be --
   MS: 133 (11.1);--

Column 5, line 30 "(8,7);40(10.6);" should be --
   (8.7);40(10.6);--

Column 5, lines 32-33 "[b-]pyrazine" should be --
   [b]pyrazine--

Column 5, line 43 "yeild" should be --yield--

Column 5, line 62 "2,86 (2H,t); 3,44 (2H,m);" should be --
   2.86 (2H,t); 3.44 (2H,m);--

Column 6, line 34 "orgaoleptic" should be --organoleptic--

Signed and Sealed this

Twenty-first Day of September 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,968,212
DATED : July 6, 1976
INVENTOR(S) : Ivon A. Flament

It is certified that error appears in the above–identified patent and that said Letters Patent are hereby corrected as shown below:

Column 6, line 66 in claim 1, please insert after "consisting essentially" the word "of"

Signed and Sealed this

Eleventh Day of January 1977

[SEAL]

Attest:

RUTH C. MASON
Attesting Officer

C. MARSHALL DANN
Commissioner of Patents and Trademarks